(12) United States Patent
Heinzle

(10) Patent No.: US 11,400,474 B2
(45) Date of Patent: Aug. 2, 2022

(54) LIQUID DISPENSER WITH BOTTLE VENTILATION

(71) Applicant: Aptar Radolfzell GmbH, Radolfzell (DE)

(72) Inventor: Christian Heinzle, Singen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 17/071,201

(22) Filed: Oct. 15, 2020

(65) Prior Publication Data

US 2021/0146391 A1 May 20, 2021

(30) Foreign Application Priority Data

Nov. 15, 2019 (EP) ..................................... 19209529

(51) Int. Cl.
*B05B 11/00* (2006.01)

(52) U.S. Cl.
CPC ...... *B05B 11/3087* (2013.01); *B05B 11/3052* (2013.01); *B05B 11/0044* (2018.08); *B05B 11/3073* (2013.01)

(58) Field of Classification Search
CPC ............. B05B 11/3087; B05B 11/3052; B05B 11/0044; B05B 11/3073
See application file for complete search history.

(56) References Cited

U.S. PATENT DOCUMENTS

| 4,694,976 | A | * | 9/1987 | Schuetz | ................. | A45D 34/00 |
| | | | | | | 222/189.11 |
| 5,709,325 | A | | 1/1998 | Renault et al. | | |
| 5,927,559 | A | * | 7/1999 | Bommer | ........... | B05B 11/00444 |
| | | | | | | 222/189.09 |

(Continued)

FOREIGN PATENT DOCUMENTS

| CN | 104684654 A | 6/2015 |
| CN | 106029239 A | 10/2016 |

(Continued)

OTHER PUBLICATIONS

Office Action of European Patent Office issued in corresponding European Patent Application No. 19 209 529.7 dated May 6, 2020 (7 pages).

(Continued)

*Primary Examiner* — Jeremy Carroll
(74) *Attorney, Agent, or Firm* — Flynn Thiel, P.C.

(57) ABSTRACT

Liquid dispenser having a liquid store and a discharge device fitted thereto and having a discharge opening. The discharge device has a pump device with a pump chamber variable in terms of volume and connected at an input side in a communicating manner to the liquid store and at an output side in a communicating manner to the discharge opening. The pump device conveys liquid from the liquid store to the discharge opening. The discharge device has a ventilation channel, by which an incoming air flow is enabled for pressure compensation between the liquid store and a surrounding atmosphere. The ventilation channel has a venti- (Continued)

lation valve openable by manual actuation of the pump device and closed when the pump device is not actuated. Further, the ventilation channel has a capillary channel portion through which the incoming air flow reaches the liquid store.

20 Claims, 4 Drawing Sheets

(56) References Cited

U.S. PATENT DOCUMENTS

| | | | |
|---|---|---|---|
| 8,454,828 | B2 | 6/2013 | Wochele et al. |
| 9,211,557 | B2* | 12/2015 | Syson ............... B05B 11/00442 |
| 9,296,003 | B2 | 3/2016 | Zavarella et al. |
| 9,468,941 | B2 | 10/2016 | Bruder et al. |
| 11,213,843 | B2 | 1/2022 | Baumann |
| 2005/0127107 | A1* | 6/2005 | Mbonyumuhire .. B05B 11/0044 222/383.1 |
| 2007/0262090 | A1* | 11/2007 | Ritsche ............... B05B 11/0044 222/189.09 |
| 2009/0026289 | A1* | 1/2009 | Nadler ................ B05B 11/3016 239/333 |
| 2009/0294347 | A1 | 12/2009 | Wochele et al. |
| 2010/0147899 | A1* | 6/2010 | Nardi .................... B65D 47/18 222/420 |

FOREIGN PATENT DOCUMENTS

| | | |
|---|---|---|
| DE | 69500443 T2 | 11/1997 |
| EP | 2130610 A1 | 12/2009 |
| EP | 3427839 A1 | 1/2019 |
| WO | 2007096049 A2 | 8/2007 |

OTHER PUBLICATIONS

Chinese Office Action with partial English translation issued in corresponding Chinese Application No. 202011271650.1 dated Dec. 29, 2021 (11 pages).

* cited by examiner

LIQUID DISPENSER WITH BOTTLE VENTILATION

CROSS-REFERENCE TO RELATED APPLICATIONS

This claims priority from European Application No. 19209529.7, filed Nov. 15, 2019, the disclosure of which is hereby incorporated by reference in its entirety.

APPLICATION FIELD AND PRIOR ART

The invention relates to a liquid dispenser, in particular for discharging pharmaceutical or cosmetic liquids. Such a liquid dispenser may, for example, be constructed in order to discharge the liquid in the form of droplets, in the form of a spray mist or in the form of a jet.

A liquid dispenser according to the invention has in the same manner as a generic liquid dispenser a liquid store for storing liquid prior to discharge and a discharge device which is fitted to the liquid store and which has a discharge opening for discharging the liquid. Furthermore, the liquid dispenser has a pump device for manual actuation having a pump chamber which can be changed in terms of volume and which is connected at an input side in a communicating manner to the liquid store and at an output side in a communicating manner to the discharge opening so that liquid can be discharged from the liquid store into a surrounding atmosphere or onto a surface.

As a result of the discharge of liquid, the liquid store empties gradually. In order to break down again or at least to decrease a reduced pressure thereby produced in the liquid store, generic liquid stores and liquid stores according to the invention have a discharge device which themselves have a ventilation channel by means of which an incoming air flow for pressure compensation between the liquid store and a surrounding atmosphere is enabled. In this instance, there are known both embodiments in which incoming air reaches a surrounding region which is separated from the liquid by a deformable bag wall and ones in which the incoming air directly reaches the region of the liquid stored in the liquid store.

The ventilation channel, particularly in embodiments in which the air directly reaches the region of the liquid, represents a possible source of disruption since the liquid may flow out through the ventilation channel, particularly when the liquid dispenser is located in the inverted position, for example, in luggage.

Problem and Solution

An object of the invention is to provide a generic liquid dispenser which reduces the risk of leakage.

To this end, it is proposed according to the invention that the ventilation channel have a ventilation valve which can be opened by means of manual actuation of the pump device and which is closed when the pump device is not actuated, and a capillary channel portion, through which the incoming air flow reaches the liquid store.

In the closed state, the ventilation channel prevents the influx of air and consequently also the discharge of liquid which has been introduced into the ventilation channel in an undesirable manner. In order to construct the ventilation channel, it is preferably formed by means of mutually opposed valve faces in particular on rigid housing components which are in abutment with each other in an end position and which consequently close the ventilation valve.

Preferably, the discharge device has a return spring which is used in particular to return the pump device in a starting position. This return spring preferably further acts at the same time as a valve spring whose resilient force presses the valve faces against each other. The valve faces of the ventilation valve are preferably in abutment with each other with a mean pressing pressure of from 0.5 N/mm$^2$ to 1.5 N/mm$^2$. The configuration of the spring is preferably carried out primarily with respect to the desired actuation force. It is therefore only possible in a limited manner to increase the sealing action of the ventilation valve. An economically advantageous ventilation valve is therefore, where applicable, configured in such a manner that it is not completely ensured that the closure action of the valve is still also excellent after a relatively long period of use.

In order also to nonetheless prevent a leakage in liquid dispensers which in the delivery state already have a ventilation valve which does not completely seal or in which after a relatively long period of use or idle time the closure effect of the valve decreases, there is provided in addition to the valve the mentioned capillary channel portion which, even in the event of a ventilation valve which still has only a limited effect, can generally prevent or at least delay the leakage of liquid.

The capillary channel portion is a part of the ventilation channel. As a result of the comparatively significant length thereof and/or as a result of a smaller cross-section or as a result of the resultant high flow resistance, it delays the undesirable discharge of liquid significantly. The capillary channel portion has a minimum clear cross-sectional surface-area which at the narrowest location of the ventilation channel is a maximum of 0.1 mm. In a particularly preferred manner, the cross-section of the capillary channel portion has at least a length of 10 mm, preferably at least a length of 30 mm and in a particularly preferred manner at least a length of 50 mm.

The mean cross-sectional surface-area of the capillary channel portion, in particular with respect to a part-portion of at least 10 mm in length, is preferably less than 0.05 mm$^2$, preferably less than 0.02 mm$^2$, particularly preferably less than 0.01 mm$^2$.

Preferably, the capillary channel portion has at least one location at which the clear cross-sectional surface-area is less than 0.02 mm$^2$. This caused a significant delay in the undesirable discharge of liquid through the ventilation channel.

The capillary channel portion preferably has, with particular respect to a part-portion of at least 10 mm in length, a quotient of the length of the capillary channel portion or this part-portion divided by the mean cross-sectional surface-area thereof which is greater than 300 mm$^{-1}$, in particular greater than 1000 mm$^{-1}$.

It is preferable for the ventilation valve to be formed by peripheral valve faces of the discharge device so that when opening there is formed a peripheral gap through which air can flow in an unimpeded manner. A particularly low flow resistance is thereby achieved at the ventilation valve so that, even in the event of only brief opening of the ventilation valve, this does not stand in the way of the pressure compensation.

A dispenser according to the invention preferably has a base at the side of the liquid store and a discharge head which can be displaced relative to the base for the purposes of operating the pump device. In this instance, the discharge opening is preferably also provided in the discharge head.

The base and the discharge head preferably have a first housing portion and a second housing portion of a rigid plastics material, wherein the first housing portion is provided on the base and the second housing portion is provided on the discharge head. In the case of the base, the rigid housing portion is preferably one which at the same time also forms a coupling device for coupling to the liquid store, for example, in the form of a snap-fitting device or a thread.

Such rigid housing portions are in the context of the invention intended to be understood to be housing portions which are produced from a plastics material with an elasticity modulus of more than 100 N/mm$^2$, preferably at least 200 N/mm$^2$, in a particularly preferred manner at least 800 N/mm$^2$. A rigid material such as, for example, PP or LDPE is suitable for most requirements of the discharge head and is also conventional. For valve faces of a ventilation valve which forms the single leakage protection, however, it is in most cases too rigid since low tolerances in the components may already be responsible for the fact that there is no longer a planar abutment of the valve faces.

The ventilation valve is preferably formed by a first valve face and a second valve face which are provided on the first and second housing portions, wherein the valve faces are in abutment with each other when the pump device is not actuated. In a particularly preferred manner, the first housing portion and the second housing portion together form a stop which prevents the discharge head from being removed from the base. In this instance in particular, the valve faces may themselves form stop faces of the stop.

The stop faces, and consequently also the valve faces which are identical thereto, are usually pressed against each other by the already-mentioned return spring.

In an embodiment according to the invention, the capillary channel portion is generally arranged with respect to an influx direction of the air downstream of the ventilation valve. Although in principle a transposed sequence is also possible, in particular in order to produce ambient pressure with only a short activation in an intermediate space which will be further described below, it is advantageous for the ventilation channel to begin upstream with the ventilation valve.

It is preferable for the pump device of a liquid dispenser according to the invention to have a cylindrical pump chamber wall and a pump piston which can be displaced inside the pump chamber wall. In such an embodiment, the ventilation valve may be arranged within the pump chamber wall, particularly when the ventilation channel extends partially through the pump piston.

However, it is preferable for the ventilation valve to be arranged at the outer side of the pump chamber wall, in particular in the region of the above-mentioned stop. A ventilation valve which is separated from the pump device in such a manner can be configured in a structurally simpler manner. It may be formed particularly by valve faces of which at least one valve face is provided at the distal end of an annular web which concentrically surrounds the pump chamber.

The capillary channel portion is preferably arranged between two sleeve components which are connected to each other in a non-positive-locking or positive-locking manner. The two sleeve components in each case form walls of the capillary channel portion.

The two sleeve components preferably have in the region of the capillary channel portion cylindrical part-portions (opening angle<1°) which are provided at one side or at both sides with recesses which form the capillary channel portion. It is also possible for the capillary channel portion to be provided in the region of conical part-portions (opening angle≥1°) of the sleeve components. This can simplify the introduction of the at least one-sided recesses when the sleeve components are produced as plastics material injection-moulded components, for example, by introducing a type of graduation on a sleeve component, which, as a result of the second sleeve component, brings about a triangular cross-section of the capillary channel portion.

In a particularly preferred manner, the capillary channel portion has a helical shape, by the portion surrounding the inner sleeve component in a helical manner. In the case of the provision of the capillary channel portion in the region of conical shaping of the sleeve components, a helical shape with a decreasing diameter is produced.

In addition to the ventilation valve which is provided according to the invention and the capillary channel which is provided according to the invention, the ventilation channel is preferably provided around a filter as a third component which also counteracts a leakage of the liquid dispenser. This filter is preferably provided with respect to the influx direction downstream of the ventilation valve and the capillary channel portion.

The filter which may in particular be a membrane filter already prevents, as a result of this arrangement, the influx of liquid into the capillary channel in a manner which is already very reliable. The pore size of the filter may be sized in such a manner that liquid can generally only pass through the filter at very low ambient pressure.

In order to prevent liquid from permanently abutting or remaining on the filter when the dispenser is moved from a horizontal position into the upright position again, it is advantageous for the filter to be constructed in a hydrophobic manner at least at the side facing in the direction of the liquid store. Such hydrophobicity is intended to be understood to be a contact angle with water of at least 90°, preferably at least 110°.

The ventilation valve and the capillary channel portion cooperate when air flows into the liquid store in such a manner that the reduced pressure of the liquid store acting through the capillary channel portion brings about an influx into the capillary channel portion of air which has previously flowed past the ventilation valve. As a result of the high flow resistance, however, the pressure compensation which is brought about by the capillary channel portion is carried out slowly.

In order to enable, in spite of the generally only brief opening of the ventilation valve, a sufficient pressure compensation to be able to take place, it is preferable for there to be provided in the ventilation channel an intermediate chamber which acts as a buffer chamber and which is arranged in particular between the capillary channel portion and the ventilation valve.

This intermediate chamber, even after the closure of the ventilation valve, still brings about a pressure compensation in the liquid state, that is to say, by means of an equalization of the pressure between the liquid store and the intermediate chamber. If the ventilation valve is opened, there is generally immediately produced a pressure compensation in the intermediate chamber since the flow resistance between the surrounding atmosphere and the intermediate chamber is very low when the ventilation valve is open. After the ventilation valve has been closed, there is initially ambient pressure in the intermediate chamber until as a result of the capillary channel portion a pressure equalization with respect to the liquid store starts.

In a particularly preferred manner, the intermediate chamber has a volume which is adapted to the pump stroke volume of the pump device. The pump stroke volume is intended to be understood to be the liquid volume which can be discharged by the pump device at a maximum in the event of actuation. The volume of the intermediate chamber is preferably at least 0.5 times this pump stroke volume. Assuming that the pressure compensation of the liquid store is carried out exclusively after the closure of the ventilation valve, in order nonetheless to achieve at least extensive pressure compensation the volume of the intermediate chamber, which is understood in particular to be the total volume between the ventilation valve and the capillary channel portion, is preferably at least the pump volume. In order, even in the event of a discharge with a plurality of pump strokes, to achieve adequate compensation, it is preferable for the volume of the intermediate chamber to correspond to at least 2 times, in a particularly preferred manner at least 5 times, the pump stroke volume of the pump device.

The pump stroke volume of the pump device is preferably between 0.01 ml and 0.25 ml, in particular between 0.05 ml and 0.15 ml. The volume of the intermediate chamber is preferably at least 0.005 ml, particularly preferably at least 0.02 ml.

A liquid dispenser according to the invention is preferably used in particular to discharge a cosmetic liquid or a pharmaceutical liquid. The liquid dispenser according to the invention is preferably therefore in a delivery state filled with such a liquid.

Pharmaceutical liquids in the liquid store may in particular be a nasal spray liquid, in particular with the active ingredient metazoline, a liquid with the active ingredient triptane, a saline solution, a liquid with a pain-relieving active ingredient, a liquid with antihistamine, a liquid with an anitallergenic agent, an eye drop or eye spray liquid, a liquid for discharge as a dermal or oral spray, an inhalation liquid, a disinfecting spray liquid or a liquid for washing wounds.

Cosmetic liquids in the liquid store may in particular be soap or lotions. The cosmetic liquids further include perfumes, skin cleansing fluids and make-up remover.

BRIEF DESCRIPTION OF THE DRAWINGS

Other advantages and aspects of the invention will be appreciated from the claims and the following description of preferred embodiments of the invention which are explained below with reference to the Figures.

DETAILED DESCRIPTION OF THE EMBODIMENTS

Figures 1A, 1B:
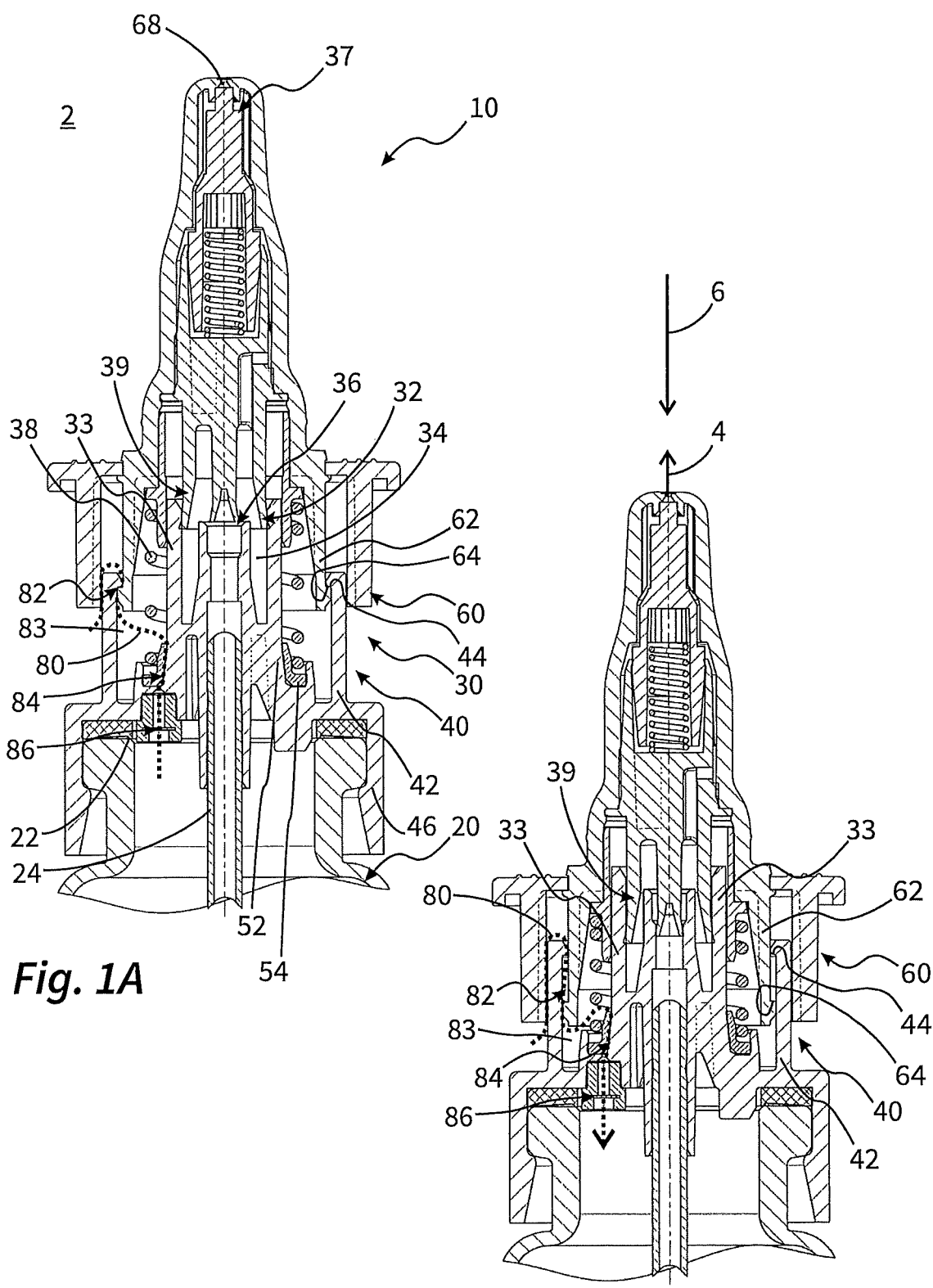
FIG. 1A shows a nasal dispenser according to the invention in an idle state with a closed ventilation channel.
FIG. 1B shows the nasal dispenser in the actuated state with an open ventilation channel.

FIGS. 1A and 1B show a liquid dispenser 10 having an only partially illustrated liquid store 20 on which a discharge device 30 is placed. The liquid dispenser 10 of FIGS. 1A and 1B is constructed as a nasal dispenser. The discharge device 30 has a base 40 which is secured to the liquid store 20 by means of a snap-ring 46, wherein, as a result of a seal 22, liquid is prevented from being able to escape from the liquid store past the discharge device 30.

In addition to the base 40, the discharge device 30 has a discharge head 60 which can be pressed down in the direction of the arrow 6 of FIG. 1B and at the distal end of which the discharge opening 68 is provided. Together, the base 40 and the discharge head 60 which can be moved relative thereto form a pump device 32. This pump device has at the side of the base a pump chamber wall 33, inside which a pump piston 39 which belongs to the discharge head 60 can be moved so that, as a result of this movement, the volume of the pump chamber 34 can be reduced counter to the force of a return spring 38. The pump device 32 has two valves, that is to say, an inlet valve 36 and a resiliently preloaded outlet valve 37. If, when the pump chamber 34 is filled, the discharge head 60 is pressed down in the manner illustrated in FIG. 1B, the inlet valve 36 is thereby closed so that a continued downward movement of the discharge head 60 in the direction of the arrow 6 leads to a pressure increase of the liquid in the pump chamber 34 which in turn brings about an opening of the outlet valve and a discharge of the liquid in the direction of the arrow 4. During the return stroke, additional liquid is drawn into the pump chamber 34 through a riser pipe 24.

During a liquid discharge, in particular a liquid discharge with a plurality of pump strokes which follow immediately one after the other, a reduced pressure is produced in the liquid store 20. In order to dissipate this reduced pressure, there is provided a ventilation channel 80 which is illustrated in FIGS. 1A and 1B by means of a dotted line and which in the state of FIG. 1A is closed and in the state of FIG. 1B is open.

With respect to FIG. 1A, this ventilation channel extends through an annular gap at the inner side of a finger support of the discharge head 60 as far as a ventilation valve 82 which is formed by stop faces 44, 64 of the base 40 and the discharge head 60. This is adjoined by an annular intermediate chamber 83 which in this instance has approximately five times the volume of a pump stroke of the pump device 32. Further downstream in the ventilation channel 80 there follows a capillary channel portion which is formed between two sleeve components 52, 54. The sleeve component 52 is identical to a main component of the base 40. The sleeve component 54 is formed by a separate sleeve which is fitted on the sleeve component 52 and which remains in position here in a non-positive-locking manner. In a manner which cannot be clearly seen in FIGS. 1A and 1B, a helical groove is introduced in the inner side of the sleeve component 54 and, after the non-positive-locking pressing on the inner sleeve component 52 forms the helical capillary channel portion. This capillary channel portion has a length of approximately 40 mm and a clear width of approximately 0.02 mm.

Further downstream in the ventilation channel 80, as a last element upstream of the liquid store, there is a filter 86 whose side facing the liquid store 20 is constructed in a hydrophobic manner.

In the idle state of the liquid dispenser 10, the ventilation valve 82 is closed in the manner described. If the liquid dispenser is now actuated and liquid is discharged in the manner described in the introduction, a reduced pressure is produced during the return stroke in the liquid store 20 and is initially not compensated for. Only in the minutes after using the dispenser and when the ventilation valve 82 has already been closed again is a compensation carried out, that is to say, as a result of the fact that air from the intermediate chamber 83, via the capillary channel portion 84 and the filter 86, reaches the liquid store 20. Although this does not lead to a complete pressure compensation in the liquid store 20, it does lead to an extensive one. After a relatively long rest period, there consequently remains a substantially uniform slightly reduced pressure both in the liquid store 20 and in the intermediate chamber 83. If the dispenser is now operated a next time, the reduced pressure in the liquid store 20 increases again during the return stroke. At the same time, however, as a result of the ventilation valve 82 which is open in accordance with FIG. 1B, there is directly produced a complete pressure compensation in the intermediate chamber 83. After the ventilation valve 82 has been closed again, an extensive pressure compensation in the liquid store as a result of the influx of air from the intermediate chamber 83 can consequently take place in the manner already described.

Figure 2:
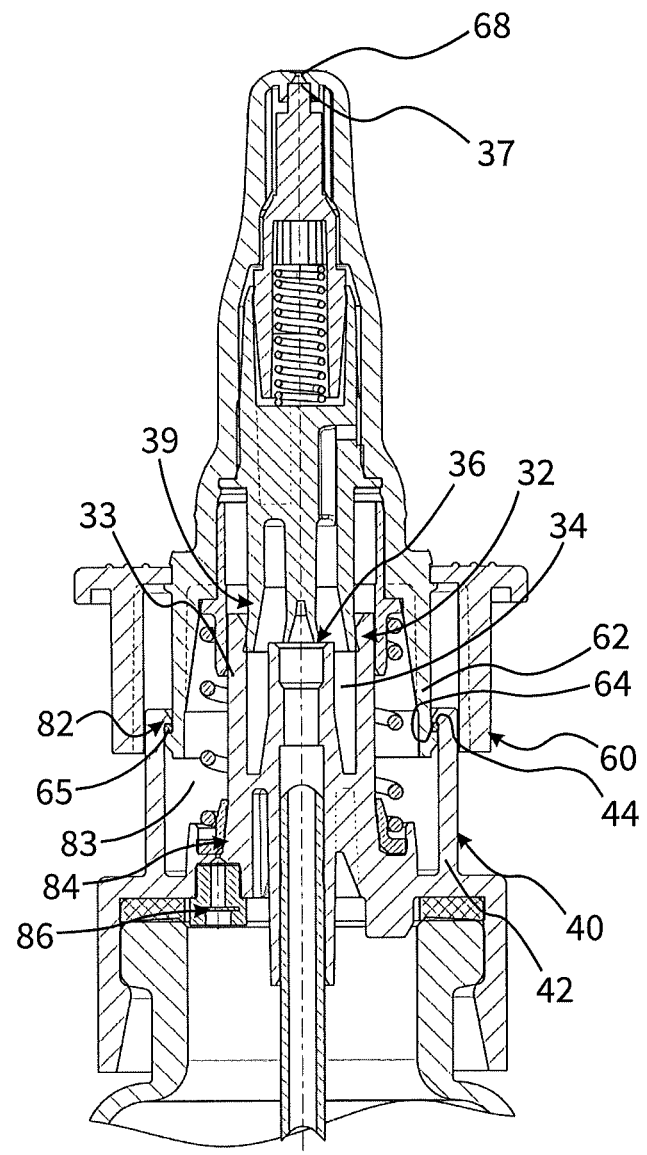
FIG. 2 shows an alternative embodiment of the nasal dispenser of FIGS. 1A and 1B with an improved ventilation valve.

FIG. 2 shows a variant of the embodiment of FIGS. 1A and 1B. The only difference is that, in this embodiment, on the ventilation valve a sealing ring 65 of resiliently deformable material, such as in particular a rubber-like material, is provided. This sealing ring 65 may either be securely provided on the base 40 or securely provided on the discharge head 60. The sealing ring improves the sealing action of the ventilation valve 82 so that it is ensured to a greater degree that the ventilation valve 82 closes in a completely tight manner even after a relatively long period of storage or idle period. Although such an embodiment is technically advantageous, it is usually economically disadvantageous. The additional sealing ring involves costs which are not necessary per se with the embodiment according to the earlier-described embodiment. As a result of the elements of the ventilation valve, which are arranged one behind the other in series, and the capillary channel and the additional filter, a discharge protection is also ensured when the ventilation valve 82 does not completely close.

Figure 3:
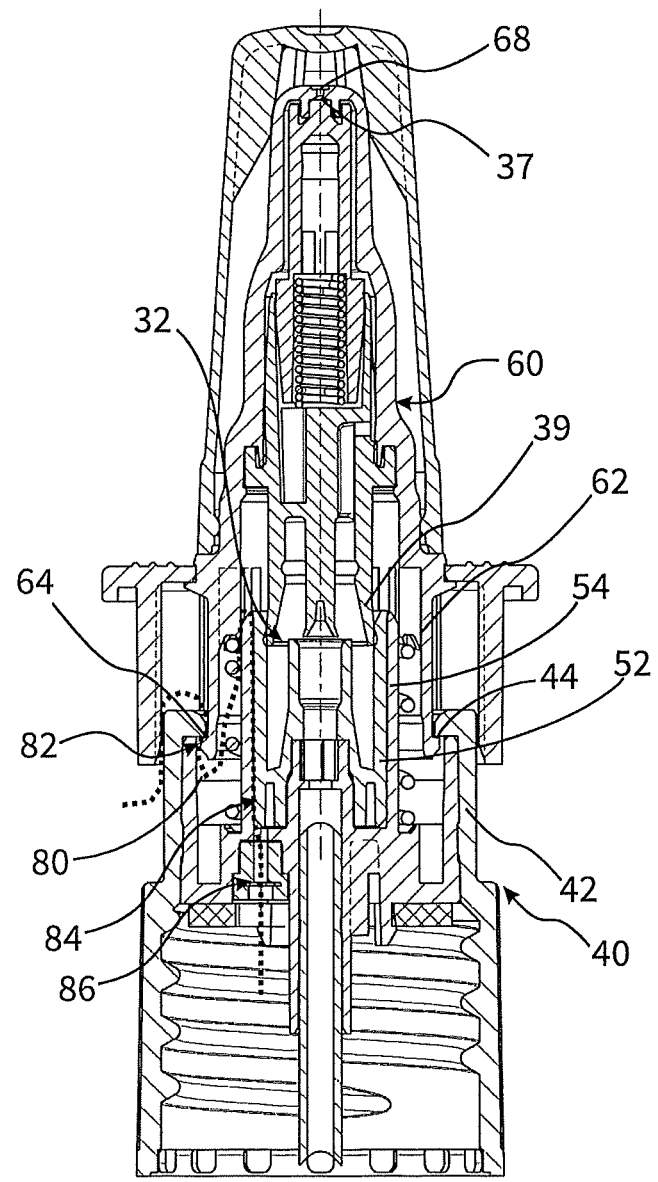
FIG. 3 shows another alternative embodiment with a differently guided ventilation channel.

FIG. 3 shows another variant of a liquid dispenser according to the invention, wherein in this instance for reasons of simplification only the discharge device 30 of the liquid dispenser is illustrated. The significant difference compared with the embodiment of FIGS. 1A and 1B is that the capillary channel portion 84 is constructed in another manner in this instance. As can be seen in the FIG. 3, the capillary channel portion 84 is formed by two sleeve components 52, 54, wherein the inner sleeve component 52 is constructed as a separate component and with the inner side thereof provides a running face for the pump piston 39. On the outer side of this inner sleeve component 52, a helical groove which forms the capillary channel portion is introduced again.

Figure 4:
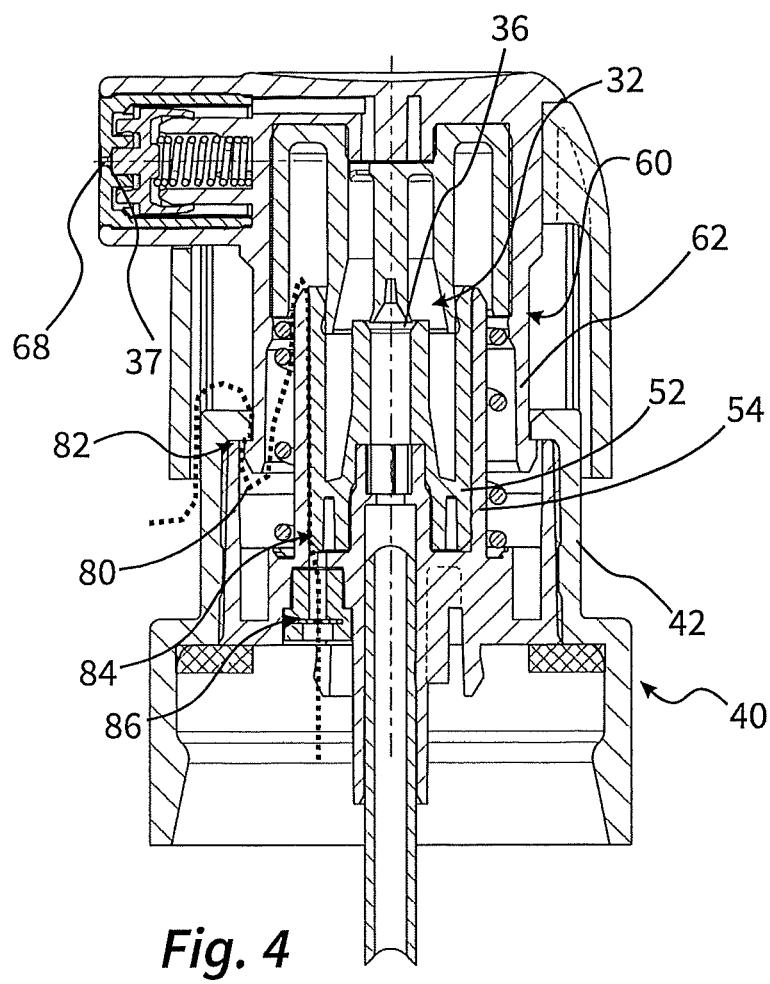
FIG. 4 shows the discharge head of a spray dispenser with a laterally orientated discharge opening.

The embodiment of FIG. 4 is, with regard to the components significant to the invention, almost identical to the embodiment of FIG. 3. In this instance, however, it is not a nasal dispenser, but instead a dispenser for laterally discharging liquid which is formed in a manner according to the invention with a ventilation channel 80.

Figure 5A:
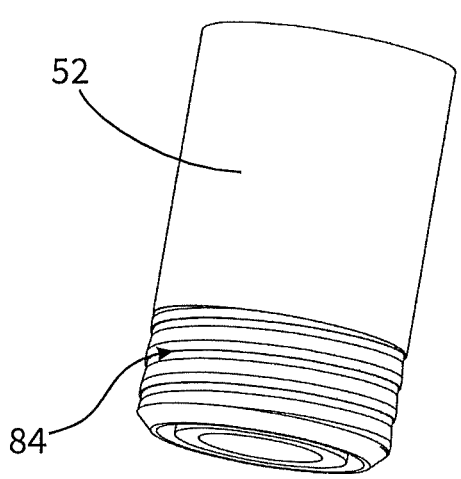
FIGS. 5A and 5B show a sleeve component for forming a capillary channel portion of the ventilation channel.
Figure 5B:
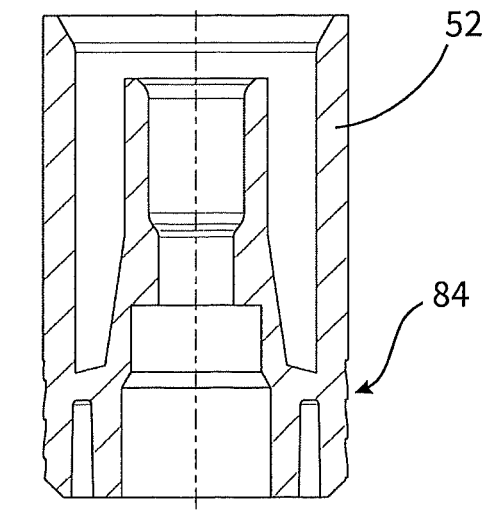

FIGS. 5A and 5B show the sleeve component 52 of the liquid dispenser according to FIG. 3, wherein the differences with respect to the corresponding sleeve component 54 of the embodiment of FIG. 4 constitute details which are not significant to the invention. It may be seen that the sleeve component 52 is provided at the lower end thereof with a helical recess which in cooperation with the inner side of the sleeve component 52 leads to a helical ventilation channel.

The invention claimed is:

1. A liquid dispenser comprising:
a liquid store for storing liquid prior to discharge;
a discharge device fitted to said liquid store and having a discharge opening for discharging the liquid; and
a manually-actuated pump device, said pump device comprising a pump chamber variable in terms of volume and having an input side connected in a communicating manner to said liquid store and an output side connected in a communicating manner to said discharge opening;
said discharge device comprising:
a ventilation channel configured to enable an incoming air flow for pressure compensation between said liquid store and a surrounding atmosphere, said ventilation channel having a ventilation valve which opens via manual actuation of said pump device and which closes when said pump device is not actuated, said ventilation channel having a capillary channel portion and the incoming air flow reaches said liquid store through said capillary channel portion;
a base disposed at a side of said liquid store, said base including a first housing portion comprising a rigid plastics material and forming a first valve face thereon; and
a discharge head, said discharge head being displaceable relative to said base for actuating said pump device, said discharge head including a second housing portion comprising a rigid plastics material and forming a second valve face thereon, said first valve face of said base and said second valve face of said discharge head together forming said ventilation valve, and said first and second valve faces are disposed in abutting relation with one another when said pump device is not actuated.

2. The liquid dispenser of claim 1, wherein said first housing portion and said second housing portion together form a stop configured to prevent removal of said discharge head from said base.

3. The liquid dispenser of claim 2, wherein said first and second valve faces form respective stop faces of said stop and abut one another to prevent removal of said discharge head from said base.

4. The liquid dispenser of claim 1, wherein said capillary channel portion is disposed downstream, with respect to a direction of the incoming air flow from the surrounding atmosphere through said ventilation channel, of said ventilation valve.

5. The liquid dispenser of claim 1, wherein said pump device comprises a pump chamber wall defining at least part of said pump chamber, and a pump piston slidably disposed within said pump chamber wall, said ventilation valve being disposed outside of said pump chamber wall.

6. The liquid dispenser of claim 1, wherein:
said capillary channel portion has a length of greater than 10 mm; and/or
said capillary channel portion has a mean cross-sectional surface area less than 0.05 mm$^2$; and/or
said capillary channel portion has a minimum clear cross-section less than 0.02 mm$^2$; and/or
a quotient of the length of said capillary channel portion divided by the mean cross-sectional surface area is greater than 300 mm$^{-1}$.

7. The liquid dispenser of claim 1, wherein said base comprises a first sleeve component and a second sleeve component disposed in surrounding relation with said first sleeve component, said capillary channel portion being disposed between said first and second sleeve components and said first and second sleeve components being connected to one another in a locking manner.

8. The liquid dispenser of claim 1, wherein said discharge device further comprises a filter disposed downstream, with respect to a direction of the incoming air flow from the surrounding atmosphere through said ventilation channel, of said ventilation valve and/or downstream of said capillary channel portion.

9. The liquid dispenser of claim 8, wherein said filter has a side disposed in facing relation with said liquid store, said side comprising a hydrophobic filter.

10. The liquid dispenser of claim 1, wherein said ventilation channel comprises an intermediate chamber disposed in said base between said capillary channel portion and said ventilation valve, said intermediate chamber having a volume corresponding to at least 0.5 times a pump stroke volume of said pump device.

11. The liquid dispenser of claim 1, wherein a pump stroke volume of said pump device is between 0.01 ml and 0.25 ml.

12. The liquid dispenser of claim 1, wherein said pump device comprises a return spring disposed to bias said first and second valve faces of said ventilation valve in abutting relation with one another.

13. The liquid dispenser of claim 12, wherein said return spring biases said first and second valve faces against one another with a mean pressing pressure of from $0.5 \text{ N/mm}^2$ to $1.5 \text{ N/mm}^2$.

14. The liquid dispenser of claim 1, wherein said liquid store is filled with a pharmaceutical liquid or a cosmetic liquid.

15. The liquid dispenser of claim 1, wherein said pump device includes a pump wall disposed on one of said base or said discharge head and a pump piston disposed on the other of said base or said discharge head, said pump wall defining at least part of said pump chamber, said pump device being manually actuable via displacement of said discharge head relative to said base which varies the volume of said pump chamber by displacing said pump piston within said pump chamber, said ventilation valve being disposed in said ventilation channel outside of said pump chamber.

16. The liquid dispenser of claim 1, wherein said ventilation valve is disposed outside of said pump chamber.

17. The liquid dispenser of claim 1, wherein manual displacement of said discharge head relative to said base actuates said pump device and causes said first and second valve faces to be in spaced-apart relation with one another to define an open configuration of said ventilation valve, said ventilation valve in said open configuration allowing air from the surrounding atmosphere to enter into said liquid store.

18. A liquid dispenser comprising:
a liquid store having an interior configured to store liquid prior to discharge from said liquid dispenser; and
a discharge device comprising:
a base secured to an open end of said liquid store, said base including a first housing portion comprising a rigid plastics material and forming a first valve face thereon;
a discharge head supported on said base for displacement relative thereto, said discharge head defining a discharge opening in communication with said interior of said liquid store for dispensing liquid from said liquid dispenser, said discharge head including a second housing portion comprising a rigid plastics material and forming a second valve face thereon;
said base and said discharge head together forming a pump device, said pump device including a pump wall disposed on one of said base or said discharge head and a pump piston disposed on the other of said base and said discharge head, said pump wall defining at least part of a pump chamber having an input side in communication with said interior of said liquid store and an output side in communication with said discharge opening, said pump device being manually actuable via displacement of said discharge head relative to said base which varies a volume of said pump chamber by displacing said piston within said pump chamber;
a ventilation channel interconnecting said interior of said liquid store with the atmosphere, said ventilation channel including a capillary channel portion disposed adjacent said liquid store; and
a ventilation valve disposed in said ventilation channel outside of said pump chamber, said first valve face of said base and said second valve face of said discharge head together forming said ventilation valve, said first and second valve faces being disposed in abutting relation with one another to define a closed configuration of said ventilation valve, and manual displacement of said discharge head relative to said base actuates said pump device and causes said first and second valve faces to be in spaced-apart relation with one another to define an open configuration of said ventilation valve, said ventilation valve in said open configuration allowing air from an atmosphere surrounding said liquid dispenser to enter into said liquid store.

19. The liquid dispenser of claim 18, wherein said ventilation channel has an upstream portion defined between said discharge head and said base, said upstream portion opening at an exterior of said liquid dispenser, said ventilation valve being disposed downstream, with respect to a direction of incoming air flow from the atmosphere and through said ventilation channel, of said upstream portion.

20. The liquid dispenser of claim 19, wherein said ventilation channel includes an intermediate portion disposed downstream of said ventilation valve and upstream of said capillary channel portion, said intermediate portion being annular in configuration and disposed in surrounding relation with said pump wall.

* * * * *